(12) United States Patent
Karolchyk

(10) Patent No.: US 12,220,397 B2
(45) Date of Patent: *Feb. 11, 2025

(54) BRAIN HEALTH FORMULATION

(71) Applicant: MEDPHARM HOLDINGS, LLC, Denver, CO (US)

(72) Inventor: Scott Karolchyk, Denver, CO (US)

(73) Assignee: MEDPHARM HOLDINGS, LLC, Denver, CO (US)

( * ) Notice: Subject to any disclaimer, the term of this patent is extended or adjusted under 35 U.S.C. 154(b) by 163 days.

This patent is subject to a terminal disclaimer.

(21) Appl. No.: 17/462,764

(22) Filed: Aug. 31, 2021

(65) Prior Publication Data

US 2021/0393578 A1 Dec. 23, 2021

Related U.S. Application Data

(63) Continuation-in-part of application No. 16/842,114, filed on Apr. 7, 2020, now Pat. No. 11,723,892.

(60) Provisional application No. 62/830,939, filed on Apr. 8, 2019.

(51) Int. Cl.
| | |
|---|---|
| *A61K 31/352* | (2006.01) |
| *A61K 9/107* | (2006.01) |
| *A61K 31/045* | (2006.01) |
| *A61K 31/047* | (2006.01) |
| *A61K 31/05* | (2006.01) |
| *A61K 36/534* | (2006.01) |
| *A61K 47/24* | (2006.01) |

(52) U.S. Cl.
CPC ............ *A61K 31/352* (2013.01); *A61K 9/107* (2013.01); *A61K 31/045* (2013.01); *A61K 31/047* (2013.01); *A61K 31/05* (2013.01); *A61K 36/534* (2013.01); *A61K 47/24* (2013.01)

(58) Field of Classification Search
CPC .... A61K 31/05; A61K 31/047; A61K 31/045; A61K 31/352
See application file for complete search history.

(56) References Cited

U.S. PATENT DOCUMENTS

| | | | |
|---|---|---|---|
| 10,912,758 B2* | 2/2021 | Firger | A61K 31/07 |
| 2004/0235770 A1* | 11/2004 | Davis | A61P 37/04 |
| | | | 435/375 |
| 2017/0283837 A1* | 10/2017 | Kavarana | C12Y 121/03 |
| 2018/0344662 A1* | 12/2018 | Eyal | A61K 45/06 |
| 2019/0015383 A1* | 1/2019 | Woelfel | A61K 31/05 |
| 2020/0138772 A1* | 5/2020 | Berl | A61K 9/0095 |

* cited by examiner

Primary Examiner — Marcos L Sznaidman
(74) Attorney, Agent, or Firm — NYEMASTER GOODE P.C.

(57) ABSTRACT

The invention relates to a unique formulation for brain health. The formulation includes a mixture of CBD, THC, THC-V, and/or flavonoids, along with at least one antioxidant, and preferably an emulsifier, spearmint extract and a film-forming agent. The formulation improves memory and cognition as well as prevents and improves symptoms in dementia and related diseases related to deterioration or loss of memory and/or cognition.

17 Claims, No Drawings

BRAIN HEALTH FORMULATION

CROSS-REFERENCE TO RELATED APPLICATIONS

This application claims the benefit of priority to U.S. Non-Provisional patent application Ser. No. 16/842,114, filed Apr. 7, 2020, entitled "BRAIN HEALTH FORMULATION," which claims the benefit of priority to U.S. Provisional Patent Application No. 62/830,939, filed Apr. 8, 2019, entitled "BRAIN HEALTH FORMULATION," the entire disclosure of which are hereby incorporated by reference in their entireties.

FIELD OF THE INVENTION

This invention relates to a brain health formulation comprising CBD, THC, THC-V, terpene(s) and nutraceuticals.

BACKGROUND OF THE INVENTION

Cannabinoids are diverse chemical compounds acting on cannabinoid receptors CB1 and CB2, among others. *Cannabis* has been used for medicinal purposes for thousands of years. Its active compounds produce pharmacological effects throughout the body, especially in the central nervous system and the immune system.

Cannabidiol (CBD) is a phytocannabinoid with promising research with its uses in treating anxiety, cognition, movement disorders, seizures, Dravet Syndrome, and pain. Its neuroprotective effects have been the subject of intensified research. Improvements in understanding of the endocannabinoid system (ECS) in many neurodegenerative and neuropsychiatric diseases, from autism to Alzheimer's, has lead scientists to further research CBD as an antioxidant and a therapeutic target in the ECS. As an antioxidant, CBD works on oxidative stress and the prevention of reactive oxygen species (ROS), or free radicals. CBD also causes an increase in other antioxidants as well, such as glutathione and superoxide dismutase. CBD works on receptor systems that control the transcription of genes in antioxidant synthesis like glutathione and superoxide dismutase, ROS elimination, mitochondrial dysfunction and inflammatory pathways.

THC (tetrahydrocannabinol) is one of at least 113 cannabinoids identified in *cannabis*. It has been shown in research to help reverse the buildup of harmful amyloid plaques within the brain that contribute to neurodegeneration through the death of brain cells. THC also reduces inflammation which contributes to brain cell damage.

THC-V, or tetrahydrocannabivarin, is a psychoactive cannabinoid found most prevalently in Sativa strains of *cannabis*. While THC-V is structurally similar to THC, they are derived from completely different parent molecules and chemical pathways. THC, along with other well-known cannabinoids including cannabidiol (CBD) and cannabichromene (CBC) are derived from cannabigerolic acid (CBGA). The parent molecule for THCV and its acidic form tetrahydrocannabivarinic acid (THCVA) is cannabigerovarinic acid (CBGVA). Both CBGVA and CBGA go through a similar reaction with a THC synthase enzyme and subsequent decarboxylation to form THCV and THC, respectively.

While THC and THC-V have been known to have psychotropic effects, to date it is not believed CBD, THC, nor THC-V have been used in the treatment or management of memory-related disorders nor for enhancement of memory or treatment of other

SUMMARY OF THE INVENTION

The invention provides the first scientifically-based formulation containing a combination of emulsified CBD, THC, and/or THC-V, terpene(s) and other unique ingredients for treatment of symptoms of dementia and related memory and cognition-related disorders, including Alzheimer's and Parkinson's diseases. The present invention is an innovative brain health formulation which allows individuals to improve and maintain memory and cognition as well as prevent and improve symptoms from existing diagnosed diseases and disorders. The addition of THC-V is believed to further reduce systemic inflammation, including in the brain, which in turn decreases the symptoms of dementia and Alzheimer's.

In addition to CBD, THC, THC-V, and terpene(s), the brain health formulation of the invention includes one or more antioxidants to suppress free radical damage and decline in brain function. The formulation further includes spearmint extract to support focus during the day without disrupting sleep at night, while the antioxidant polyphenols present in the extract promote new brain cell growth, support working memory, and improve agility and reaction performance. In addition, the formulation of the invention preferably further includes at least one film forming agent/solubilizer to enhance bioavailability of the formulation.

Other features and advantages of the invention will be apparent from and are encompassed by the following detailed description and claims.

DETAILED DESCRIPTION OF THE PREFERRED EMBODIMENT

The present invention relates to a unique brain health formulation containing at least CBD, THC and/or THC-V, one or more terpenes and, optionally, one or more flavonoids. The *cannabis* extracts of the invention are any that can be derived or extracted from *cannabis* plants, with a preference for the *Canna*-Tsu strain. *Canna*-Tsu is a hybrid *cannabis* strain that combines genetics from two CBD-rich parent strains, Cannatonic and Sour Tsunami. *Canna*-Tsu has a high-CBD, low THC cannabinoid profile. Strains high in CBD like *Canna*-Tsu are in high demand for patients for the treatment of pain, inflammation, anxiety, and seizures.

*Cannabis* plants produce a unique family of terpenophenolic compounds called cannabinoids, which produce the "high" one experiences from consuming marijuana. There are 483 identifiable chemical constituents known to exist in the *cannabis* plant, and at least 113 different cannabinoids have been isolated from the plant. The two cannabinoids usually produced in greatest abundance are cannabidiol (CBD) and/or (−)-trans-$\Delta^9$-tetrahydrocannabinol (THC), but only THC is psychoactive.

*Cannabis* plants are categorized by their chemical phenotype or "chemotype," based on the overall amount of THC produced, and on the ratio of THC to CBD. Although overall cannabinoid production is influenced by environmental factors, the THC/CBD ratio is genetically determined and remains fixed throughout the life of a plant. Non-drug plants produce relatively low levels of THC and high levels of CBD, while drug plants produce high levels of THC and low levels of CBD.

The CBD, THC and/or THC-V, one or more terpenes, and one or more flavonoids of the present invention may be obtained from *cannabis* plant extract. In addition to cannabinoids, *cannabis* plants produce terpenes, a diverse group of organic hydrocarbons that are the building blocks of the cannabinoids. Over 100 different terpenes have been identified in the *cannabis* plant, and every strain tends toward a unique terpene type and composition. The terpenes act synergistically with the cannabinoids to provide a therapeutic effect. Examples of some common terpenes found in *cannabis* include bisabolol, borneol, caryophyllene, cineole/eucalyptol, delta-3-carene, limonene, linolool, myrcene, pinene, and pulegone. In various aspects the invention provides *cannabis* extracts with predefined ratios of cannabinoids. Standard conditions for cannabinoid assays, and methods of calculating cannabinoid content (as %) are well known in the art.

The cannabinoid extract starting materials are typically mixtures of at least 95% total cannabinoids which include terpenes and/or flavonoids. Flavonoids are made up of groups of polyphenolic compounds that act as secondary metabolites to a myriad of plants and fungi. *Cannabis* contains some of the following flavonoids: cannaflavins A, B, and C, β-sitosterol, vitexin, isovitexin, apigenin, kaempferol, quercetin, luteolin, and orientin. The range of flavonoids found in *cannabis* plants varies depending on the genetics and growth conditions of the plant.

In one embodiment of the invention, the extract primarily contains THC or THC-V, CBD, one or more terpenes, and/or one or more flavonoids. As defined herein, "THC", "THC-V", and "CBD" include any CBD, THC, THC-V derivatives, salts, isomers, isoforms, polymorphs, solvates, prodrugs, chelates, and/or clathrates thereof.

Other cannabinoids and terpenes may be present in the extract as well so long as the extract contains sufficient amounts of THC, THC-V and CBD to provide the memory-enhancing aspects of the invention. Other cannabinoids typically present in the extract include tetrahydrocannabinolic acid (THCa), cannabidiolic acid (CBDa), cannabinolic acid (CBNa) cannabichromenic acid (CBCa), cannabinol (CBN), cannaberol acid, and cannabichromene (CBC). Sources of cannabinoids include all plant species of the genus *Cannabis sativa* L. (commonly called *Cannabis*) including, but not limited to, *C. sativa, C. indica*, and *C. ruderalis*.

In addition to or in the alternative, the formulation may include synthetic and/or biosynthetic sources of THC, THC-V, and/or CBD from marijuana or hemp and/or any sources thereof, including synthetic, bioengineered, genetically-modified and/or genetically-edited sources. Persons skilled in the art will further understand that these sources may include chemicals that are active at any cannabinoid receptor, as well as chemicals that modulate, synergize with, or otherwise bind or interact with any cannabinoid receptor whether natural, synthetic, semi-synthetic, derived from *cannabis*, or derived from any other species.

Persons skilled in the art will understand that these examples are not limiting to the invention but serve to illustrate the scope of the invention. The techniques described throughout this document cover all genetic variations of the plants belonging to *Cannabis sativa, Cannabis indica*, and *Cannabis ruderalis*, plants that produce any chemicals that are active at any cannabinoid receptor, and all genetic variations generated as a result of genetic deletions, single base-pair substitutions, and the introgression of nucleotide sequences from related plants that could potentially have come about through cross breeding. Also covered are any unique *Cannabis sativa, Cannabis indica*, and *Cannabis ruderalis* generated through CRISPR/Cas, selective breeding, or any other method of genetic modification such as TALEN's and zinc finger nucleases.

The invention is based upon the premise that utilizing THC-V in the formulation can dramatically decrease fasting blood sugar and systemic insulin levels in the body, thus reducing systemic inflammation, including in the brain. This reduction in brain inflammation, in turn, is believed to decrease the symptoms of dementia and Alzheimer's. THC-V further reduces glucose intolerance and provides analgesic and anti-inflammatory properties, and is neuroprotective, all of which are believed to improve brain health in accordance with the teachings of the invention.

The terpene and/or flavonoids in the extract include, but are not limited to, myrcene, alpha-bisabolol, caryophyllene, limonene, eucalyptol, nerolidol, terpineol, carene, valencene, geraniol, humulene, delta-3-carene, borneol, alpha-pinene and beta-pinene, and linalool, including natural and synthetic sources thereof.

The brain health formulation of the invention should include at least about 1 mg CBD, with about 5-50 mg being preferred, and about 30 mg being most preferred. The formulation should include at least about 1 mg THC, with about 5-25 mg being preferred, and about 5 mg being most preferred. Alternatively, or in addition to the THC, the formulation contains at least about 1 mg THC-V, with about 5-25 mg being preferred, and about 5 mg being most preferred. In one embodiment of the invention, the formulation contains both THC and THC-V in the amounts already described.

The formulation may further include at least one terpene in an amount of at least 0.01 mg, with about 0.1 mg-10 mg being preferred, and about 1.0 mg being most preferred. In one embodiment, the terpene is bisabolol. In addition, the formulation may include one or more flavonoids in an amount of at least 0.01 mg, with about 0.1 mg-10 mg being preferred, and about 1.0 mg being most preferred. In one embodiment of the invention, the flavonoid is nobiletin.

The CBD, THC, THC-V, at least one terpene and/or at least one flavonoid may be emulsified with at least one emulsifier to form a powdered extract, as more fully explained below. If included, the emulsifier is preferably a carbohydrate substrate that may include, but is not limited to, starch, maltodextrins, glucose syrup, crystalline glucose (dextrose, sucrose, fructose), caramel, sorbitol, maltitol, mannitol, isomalt, beta/hydroxylpropyl cyclodextrins, lecithin, acacia, gum Arabic, xanatan gum, carrageenan, polyglycols, locust bean gum, tapioca, carboxymethylcellulose, and combinations of the same. In one embodiment, the emulsifying system includes an oil soluble emulsifier combined with a water soluble emulsifier. In another embodiment, the emulsifying system is a combination of maltodextrin and gum arabic (acacia). If an emulsifying system is used the system includes about 1:20-20:1 water soluble emulsifier to oil soluble emulsifier. In one embodiment, the system includes about 5% by weight oil soluble emulsifier to about 95% by weight water soluble emulsifier.

The brain health formulation of the invention further includes one or more antioxidants. Antioxidants are substances that can prevent or slow damage to cells caused by free radicals. Antioxidants are well known in the art and include, but are not limited to, vitamin A, vitamin C, vitamin E, beta-carotene, lycopene, lutein, selenium, manganese, zeaxanthin, flavonoids, flavones, catechins, polyphenols, and phytoestrogens. Carotenoids are a family of naturally occurring antioxidants that have important functions for human health. In one embodiment of the invention, the formulation includes lutein and zeaxanthin. Lutein and zeaxanthin supplementation have been shown to reduce oxidative damage from free radicals in accordance with the formulations of the invention. In one embodiment, the brain health formulation includes at least about 1 mg by weight lutein, with at least about 5-20 mg lutein being preferred, and about 10 mg lutein being most preferred. In one embodiment, the formulation includes at least about 0.1 mg zeaxanthin, with about 1-5 mg being preferred, and about 2 mg being most preferred. In another embodiment of the invention, the formulation includes a ratio of about 2:1 to about 6:1 by weight lutein to zeaxanthin.

The brain health formulation of the invention also includes spearmint extract. As noted, this extract has been clinically shown in accordance with the invention to support focus during the day without disrupting sleep at night. Spearmint extract further includes polyphenols having antioxidant properties to promote new brain cell growth and support a function of the brain known as working memory, thus improving the ability to learn, manage information, and react. The polyphenols further increase neurotransmitter levels, protect neurons, and promote neural growth. The use of spearmint extract in accordance with the invention provides improved cognitive function, more productive days, increased focus, and increased agility and reaction performance. In one embodiment, the brain health formulation includes at least about 100 mg spearmint extract with at least about 250-500 mg being preferred, and about 250 mg being most preferred. In one embodiment, the formulation contains at least 80% by weight spearmint extract.

The brain health formulation of the invention may further include further a film-forming/solubilizing agent. Film-forming agents are well known in the art and may include, but are not limited to pullulan, hydroxypropylmethyl cellulose, hydroxyethyl cellulose, Span 80, polysorbate 80, hydroxypropyl cellulose, polyvinyl pyrrolidone, carboxymethyl cellulose, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, lecithin and phospholipids, dextrin, pectin, levan, elsinan, collagen, gelatin, zein, gluten, soy protein isolate, whey protein isolate, casein and mixtures thereof, in amounts ranging from at least about 0.01 wt % of the brain health formulation, and more preferably at least about 1-20 wt % of the formulation. A preferred film former for use in the invention is lecithin phospholipids.

In general, the brain health formulations of the invention may be administered to provide the following dosages of ingredients (per day):

| Ingredient | Dosage Range | Preferred Dose | Most Preferred Dose |
|---|---|---|---|
| CBD | at least 1 mg | 5-50 mg | 30 mg |
| THC | at least 1 mg | 5-25 mg | 5 mg |
| THC-V | at least 1 mg | 5-25 mg | 5 mg |
| Terpene(s) | at least 0.01 mg | 0.1-10 mg | 1.0 mg |
| Flavonoid(s) | at least 0.01 mg | 0.1-10 mg | 1.0 mg |
| Antioxidant | at least 0.1 mg | 1-20 mg | 2-10 mg |
| Lutein (optional antioxidant) | at least 1 mg | 5-20 mg | 10 mg |
| Zeananthin (optional antioxidant) | at least 0.1 mg | 1-5 mg | 2 mg |
| Spearmint extract (optional) | at least 100 mg | 250-500 mg | 250 mg |

The formulations may be administered in single or divided doses per day. In one embodiment, the formulation includes CBD 30 mg, THC 5 mg, and THC-V 5 mg and is administered once daily. In another embodiment, the formulation includes CBD 30 mg, THC 5 mg, and THC-V mg and is administered twice daily.

In forming the brain health formulation of the invention, the cannabinoid extract(s), one or more terpenes and/or one or more flavonoids, and emulsifier are first combined with a pharmaceutically acceptable solvent to form a dissolved extract. Suitable solvents for this purpose include, but are not limited to, caprylic acid triglycerides, n-hexane, ethyl acetate, diethyl ether, 2-propanol, acetone, ethanol, ethanol/water, butane, propane, benzyl alcohol, 1,3-butylene glycol, citric acid esters of mono- and di-glycerols, glycerin, glyceryl triacetate, glyceryl tributyrate, isopropyl alcohol, monoglyceride citrate, propylene glycol, triethyl citrate, and propylene glycol mono- and de-esters. In one embodiment of the invention, the solvent is caprylic acid triglyceride.

The solvent is combined with the extract in a ratio of 0.5-5.0:1.0 by weight solvent:extract, with a ratio of about 1.5-2.0:1 by weight solvent:extract being preferred, and about 1.75:1 by weight solvent:extract being most preferred. The solvent/extract mixture is preferably heated to a range of about 40-85° C. with about 50-60° C. being preferred and about 55° C. being most preferred. The mixture may optionally be stirred/agitated to more thoroughly combine the ingredients.

In one embodiment of the invention, the liquid extract is made into a water soluble, powdered extract following solubilization, such as in accordance with the teachings of U.S. Ser. No. 16/576,162 (U.S. Pat. Pub. No. 2020-0085740 A1), the disclosure of which is hereby specifically incorporated herein by reference. The powdered extract may then be formulated into various solid pharmaceuticals, including tablets, capsules, dry powder inhalers, and powdered mixes using methods well known in the art.

To form a powdered extract, once the components of the extract are dissolved in the solvent, the dissolved extract is combined with the emulsifier. In this regard, the dissolved extract may simply be combined with the emulsifier. In one embodiment, the dissolved extract is sprayed onto the emulsifier while the emulsifier is under agitation and vacuum. In a preferred embodiment, a Ross vertical cone screw blender is utilized whereby the powdered solids are combined under vacuum then immediately subjected to high sheer mixing at a point in the blender where flow is most turbulent. In another embodiment, the dissolved extract is dripped into the emulsifier while mixing. If more than one emulsifier is used in this step it is preferred to mix the emulsifiers prior to combining with the dissolved extract.

The solvent/extract mixture is next dried to form a powder by preferably heating the mixture for several hours to a range of about 50-85° C. with about 50-60° C. being preferred and about 55° C. being most preferred. The mixture may optionally be stirred/agitated during this step to more thoroughly combine the ingredients. In one embodiment, the mixture is agitated under vacuum. The solvent/extract mixture may also be dried using conventional methods including, but not limited to, air drying, spray drying, freeze drying, etc. The mixture is dried for a time period sufficient to provide a flowable powder free of aggregates, with a moisture content generally ranging from about 2-8% by weight, with about 4% moisture by weight being preferred. The powdered product may be further processed into pharmaceutical formulations and/or used for testing.

The extract of the invention (either liquid or powdered) may be formulated with any convenient pharmaceutically acceptable diluents, carriers or excipients to produce a pharmaceutical composition. The choice of diluents, carriers or excipients will depend on the desired dosage form, which may in turn be dependent on the intended route of administration to a patient. Oral dosage forms include, but are not limited to, tablets, capsules, suspensions, granules, and solutions. The pharmaceutical preparations of the present invention are manufactured in a manner which is itself well known in the art. For example, the pharmaceutical preparations may be made by means of conventional mixing, granulating, dissolving, and/or lyophilizing processes. The processes to be used will depend ultimately on the physical properties of the active ingredient used.

Suitable excipients are, in particular, fillers such as sugars for example, lactose or sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices. For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include capsules made of gelatin, as well as soft, sealed capsules made of gelatin and a plasticizer such as glycerol or sorbitol. The capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids; such as fatty oils, liquid paraffin, or liquid polyethylene glycols. In addition stabilizers may be added.

The pharmaceutical preparations of the present invention are manufactured in a manner which is itself well known in the art. For example the pharmaceutical preparations may be made by means of conventional mixing, granulating, dissolving, lyophilizing processes. Such dosage forms may be prepared in accordance with standard principles of pharmaceutical formulation, known to those skilled in the art. The extract may be formulated for oral use (e.g. capsules) in dosage forms that provide 5 mg, 10 mg, 20 mg, or 100 mg of total CBD/THC/terpene/flavonoid per dose.

The formulations of the invention are effective in improving brain health in people which includes, but is not limited to, improvement of cognitive function, preventing brain damage, slowing the progression of Alzheimer's Disease, slowing the progression of dementia, slowing the onset of dementia, lessening the symptoms of Alzheimer's Disease, lessening the symptoms of dementia, etc.

The following examples are offered to illustrate but not limit the invention. Thus, it is presented with the understanding that various formulation modifications as well as method of delivery modifications may be made and still are within the spirit of the invention.

Example 1

A pharmaceutical composition was prepared as described below. The following products were used in the amounts and concentrations specified:

| Ingredient | Amount (mg) |
| --- | --- |
| CBD | 30 |
| THC | 5 |
| Lutein | 10 |
| Zeaxanthin | 2 |
| Spearmint Extract | 250 |
| Lecithin | 25 |
| Bisabolol | 1 |
| Nobiletin | 1 |
| Total | 324 mg |

Capsules were prepared in two steps:
1. Powders were weighed and mixed in v-blender and then filled into empty capsules.
2. The liquid *cannabis* extract (prepared above) is pipetted into the capsules containing the actives powder, capsules are capped and packaged The method of using a manual capsule filling machine is as follows:
1. Open the empty capsules and place the lower halves (the 'body') in the holes of the bottom plate of the filling machine. Often machines have spacers that are inserted between the base plate and the plate with holes into which the capsules are fitted. These need to be set so that the lower body of each capsule is flush with the top of the plate that holds the capsule bodies.
2. Pipette the liquid and powder into the body of each capsule, ensuring an even distribution of powder using a spreader plate.
3. Take out the spacers and gently tap the plate with holes downwards so that each of the capsule bodies protrudes from the top of the plate.
4. Place the top half (' cap') of each capsule onto the lower half but do not press down firmly until all are in place. Once all the tops are in place, they can be pressed down gently (often a click is heard when they are all completely fitted.
5. If the machine has an upper plate into which caps can be loaded, fit these into the upper plate, and then flip the plate over and align it with the bottom plate, ensuring that all capsules halves are perfectly aligned.
6. Press the top plate firmly to secure the top of each capsule with the corresponding lower half The above process can also be automated.

The formulation is placed in a capsule for oral administration, once daily.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplishes at least all of the intended objectives.

What is claimed is:

1. A formulation for improved brain health comprising: 5-50 mg cannabidiol (CBD); 5-25 mg tetrahydrocannabinol (THC); 5-25 mg tetrahydrocannabivarin (THC-V); 0.1-10 mg of at least one terpene; 1-20 mg of at least one antioxidant; 250-500 mg spearmint; and at least one emulsifier.

2. The formulation of claim 1 further including at least one flavonoid.

3. The formulation of claim 1 whereby the at least one antioxidant is selected from the group consisting of lutein and zeaxanthin.

4. The formulation of claim 1 whereby the CBD is extracted from CannaTSU strain.

5. The formulation of claim 1 whereby the emulsifier is lecithin.

6. The formulation of claim 1 further comprising a film-forming agent.

7. The formulation of claim 1 whereby the terpene is bisabolol.

8. The formulation of claim 3 comprising about 5-20 mg lutein.

9. The formulation of claim 3 comprising about 1-5 mg zeaxanthin.

10. The formulation of claim 6 comprising between about 1-20 wt % film-forming agent.

11. A method of improving or preventing deterioration of brain health in a mammal comprising: administering to a mammal a formulation comprising 5-50 mg cannabidiol (CBD); 5-25 mg tetrahydrocannabinol (THC), 5-25 mg tetrahydrocannabivarin (THC-V), 0.1-10 mg of at least one terpene; 1-20 mg of at least one antioxidant; 250-500 mg spearmint; and at least one emulsifier at least once daily.

12. The method of claim 11 comprising the administration of at least +5 mg THC and at least +5 mg THC-V daily.

13. The method of claim 11 comprising the administration of about 5 mg THC and about 5 mg THC-V daily.

14. The method of claim 11 comprising the administration of at least 5 mg THC-V twice daily.

15. The method of claim 11 comprising the administration of about 30 mg CBD, about 5 mg THC and about 5 mg THC-V daily.

16. The formulation of claim 1 comprising at least 80% by weight spearmint extract.

17. The formulation of claim 1 whereby the formulation is emulsified with the emulsifier to provide a powdered formulation.

* * * * *